United States Patent
Nakajima et al.

(10) Patent No.: US 7,052,657 B2
(45) Date of Patent: May 30, 2006

(54) METHOD FOR CONTROLLING REACTION AND CONTROLLING APPARATUS

(75) Inventors: Hidehiko Nakajima, Himeji (JP); Yoshiyuki Harano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/257,320

(22) PCT Filed: Feb. 15, 2002

(86) PCT No.: PCT/JP02/01333

§ 371 (c)(1), (2), (4) Date: Oct. 10, 2002

(87) PCT Pub. No.: WO02/068374

PCT Pub. Date: Sep. 6, 2002

(65) Prior Publication Data

US 2003/0181760 A1    Sep. 25, 2003

(30) Foreign Application Priority Data

Feb. 28, 2001 (JP) ............................. 2001/054762

(51) Int. Cl.
F28D 51/16 (2006.01)
(52) U.S. Cl. .................... 422/198; 562/538; 560/232
(58) Field of Classification Search ............... 562/606, 562/607, 608
See application file for complete search history.

(56) References Cited

U.S. PATENT DOCUMENTS 5,352,415 A * 10/1994 Ochiai ..................... 422/105
5,374,774 A * 12/1994 Ochiai ..................... 562/519
5,550,279 A * 8/1996 Yano et al. ............... 558/277
5,973,197 A   10/1999 Denis et al.

FOREIGN PATENT DOCUMENTS

| CN | 1152301 A | 6/1997 |
|---|---|---|
| JP | 48-54011 A | 7/1973 |
| JP | 6-321847 A | 11/1994 |
| JP | 10-508594 A | 8/1998 |
| JP | 11-43677 A | 2/1999 |
| JP | 2000-95723 A | 4/2004 |

* cited by examiner

Primary Examiner—Johann Richter
Assistant Examiner—Karl Puttlitz
(74) Attorney, Agent, or Firm—Birch, Stewart, Kolasch & Birch, LLP

(57) ABSTRACT

While supplying methanol and carbon monoxide via feed lines 17 and 19, respectively, to a liquid phase reaction system 3 including a carbonylation catalytic system, and maintaining a substantially constant liquid level of the reaction system, part of the reaction mixture containing the produced acetic acid is drawn out from the reaction system and supplied to a flash distillation column 4, and the high boiling point component, which contains the carbonylation catalytic system that has been separated by ths flash distillation, is circulated to the reaction system 3 by means of a circulation line 21. At circulation line 21, the flow rate is detected by a flow rate sensor F3 and the temperature is detected by a temperature sensor T2, and based on the detection data, a control unit 8 is used to control the temperature of the circulated high boiling point component by means of a temperature regulating unit 6 and thereby to suppress temperature and pressure fluctuations of the above-mentioned reaction system.

12 Claims, 2 Drawing Sheets

METHOD FOR CONTROLLING REACTION AND CONTROLLING APPARATUS

This application is filed under 35 U.S.C. 371 and claims the benefit of PCT/JP02/01333 file Feb. 15, 2002.

TECHNICAL FIELD

This invention relates to a reaction control method (or stabilization method) and a reaction control apparatus that are useful for stabilizing a reaction system for a carbonylation reaction, etc.

BACKGROUND ART

Carboxylic acids (such as acetic acid, etc.) and derivatives thereof (such as methyl methacrylate, etc.) are produced industrially by use of carbonylation reactions. For example, Japanese Patent Application Laid-open No. 54011/1973 (JP-48-54011A) discloses a carbonylation method in which an olefin, an alcohol or ester thereof, a halide, or ether derivative is allowed to react in the liquid phase with carbon monoxide in the presence of a catalytic system containing a rhodium or iridium component and an iodine or bromine component. In this process, at least part of the liquid reactants is passed without heating through a separation zone that is substantially low in pressure to vaporize at least part of an above-mentioned carbonylation product, the vaporized carbonylation product is taken out, and the residual liquid reactants are recirculated to the above-mentioned reaction zone. With this literature, the removal of unreacted carbon monoxide from the reactor is indicated. Japanese Patent Application Laid-open No. 321847/1994 (JP-6-321847A) indicates a carbonylation product recovery method in which an iridium catalyst is used as the carbonylation catalyst, a vapor component containing the carbonylation product and a liquid component containing the iridium catalyst are generated by vaporization of the reaction product, the vapor component and the liquid component are separated, and the concentration of water in the liquid component is maintained at least at 0.5 weight %. With this literature, the discharge of unreacted carbon monoxide as exhaust gas from the reactor is illustrated.

Japanese Patent Application Laid-open No. 508594/1998 (JP-10-508594A) proposes a method comprising a first region, in which a carboxylic acid is produced by liquid phase carbonylation in the presence of a rhodium catalyst, and a second region, in which the reaction mixture is partially vaporized, and wherein a vapor fraction containing the produced carboxylic acid is refined and the non-vaporized liquid fraction containing the catalyst is circulated to the first region, carbon monoxide is added to the non-vaporized liquid fraction generated from the second region with preventing return of carbon monoxide to the second region to avoid loss of carbon monoxide.

However with such carbonylation reactions, the temperature and pressure of the reaction system fluctuate or vary with the circulation of the high boiling point component to the reaction system, causing the carbon monoxide consumption rate or usage rate of the reaction system to fluctuate and thus making the stabilization of the reaction system difficult. Also, the carbon monoxide discharge rate increases in accompaniment with the supplying of excess carbon monoxide and fluctuation of the carbon monoxide consumption rate of the reaction system. Carbon monoxide therefore could not be used effectively in the carbonylation reaction.

Japanese Patent Application Laid-open No. 95723/2000 (JP-2000-95723A) discloses a control method for a process of producing acetic acid by carbonylation, wherein the flow of carbon monoxide that passes through a control valve is measured, the average value of the carbon monoxide flow within a predetermined term is calculated, a fixed value is added to this average carbon monoxide flow to calculate the maximum flow rate of carbon monoxide, and operation is performed so that the flow rate of carbon monoxide into the reactor will not exceed the maximum flow rate. With this method, since the carbon monoxide flow rate is controlled using a maximum flow rate, determined by adding a fixed value to the average carbon monoxide flow, as a reference, it is difficult to suppress fluctuations of the temperature and pressure of the reaction system and thereby stabilize the reaction system.

Thus an object of the present invention is to provide a reaction control method (or stabilization method) and a reaction control apparatus (or stabilization apparatus) by which a liquid phase reaction system, such as a carbonylation reaction system, can be stabilized effectively.

Another object of the present invention is to provide a reaction control method (or stabilization method) and a reaction control apparatus (or stabilization apparatus) with which the temperature and pressure fluctuations of a liquid phase reaction system are controlled to enable stable production of products in an industrially advantageous manner.

DISCLOSURE OF INVENTION

The inventors of the present invention made intensive studies to achieve the above objects, and finally found that (1) even when a separated component (such as a high boiling point component or fraction, etc.), which has been separated by distillation from a carbonylation reaction mixture, is circulated (or returned) to the reaction system (i.e., the pressurized reaction system) steadily at a predetermined rate, the circulation rate (return flow rate) of the separated component will fluctuate, the temperature of the reaction system will fluctuate accordingly, the pressure of the reaction system will fluctuate in accompaniment with this temperature change even when carbon monoxide is supplied to the reaction system steadily at a predetermined rate, and the above-mentioned temperature and pressure fluctuations will be large especially in the case where the reaction temperature of an exothermic reaction system is controlled by the circulation rate (return flow rate) of the separated component and without using a cooling unit, and that (2) when the temperature of the circulated separated component is controlled according to (or depending on) the heat quantity of the separated component that is returned to the reaction system, the temperature and pressure fluctuations of the reaction system can be suppressed (or restrained) effectively, the discharge amount of carbon monoxide can be reduced to enable effective use of carbon monoxide for reaction, and the reaction system can be stabilized. The present invention was accomplished based on the above finding.

That is, the reaction control method (or stabilization method) of this invention is a method in which, while supplying reaction components continuously into a liquid-phase reaction system (e.g., a pressurized liquid-phase reaction system), part of the reaction product in the reaction system is subjected continuously to a separation step and the separated component (a high boiling point component or fraction, etc., that has been separated from a low boiling point component or fraction) that has been separated in the separation step is circulated (or returned) to the above-mentioned reaction system, wherein the temperature of the above-mentioned reaction system is controlled by controlling the heat quantity of the separated component that is circulated or returned to the reaction system in association with the circulation rate (return flow rate) of the separated component from the above-mentioned separation step. With this method, the separated component that is circulated or returned to the reaction system usually contains effective or useful components (catalytic components, etc.) that are effective for the reaction. The method of this invention can be applied favorably to a system, wherein the circulation rate (return flow rate) of a separated component (a circulated component such as a high boiling point) from the separation step to the reaction system fluctuates. With such a system, it is useful, for control of the reaction system temperature at a predetermined temperature, to detect the flow rate and temperature of the circulated separated component (the circulated component such as the high boiling point component) and to control the temperature of the circulated separated component (or circulated component) based on the detected flow rate and temperature. Though the reactor may be equipped with a heat removal unit or a cooling unit, this invention is preferably applied to an exothermic reaction system that the reactor is not equipped with a heat removal unit or cooling unit and the temperature of this exothermic reaction system (or reactor) can be controlled by the temperature and flow rate of a separated component that is lower in temperature than the reaction system (or reactor). In the present invention, usually, treatments or operations in the above-described steps may be conducted continuously or successively.

The above-described reaction control method (reaction stabilization method) can be utilized in various liquid phase reaction systems, such as carbonylation reaction systems (a pressurized carbonylation system). For example, the method can be applied to a system, wherein an alcohol and carbon monoxide are supplied into a liquid phase reaction system that comprises a carbonylation catalytic system, part of the reaction mixture comprising the carboxylic acid produced by the reaction is drawn out from the reaction system while maintaining a substantially constant liquid level of the reaction system and is subjected to a flash distillation, and a high boiling point component or fraction is circulated or returned to the reaction system, the high boiling point component comprises the carbonylation catalytic system and is separated by the flash distillation from a low boiling point component or fraction comprising the carbonylation product. The high boiling point component may contain a carbonylation catalytic system comprising a rhodium catalyst and a cocatalyst, and the low boiling point component may contain a carboxylic acid, a carboxylic acid ester and an alkane halide. With this system, the low boiling point component that has been separated by the flash distillation may be further subjected to a refining system for separating into a second low boiling point component or fraction, a component containing a carboxylic acid, and a second high boiling point component or fraction, and the second low boiling point component that has been separated by this refining system may be circulated or returned to the reaction system. With this carbonylation reaction, the second low boiling point component usually contains a cocatalyst (e.g., an alkane halide), etc. The above-mentioned liquid phase reaction system may be a reaction system in which methanol and carbon monoxide are reacted in the presence of a carbonylation catalytic system to produce acetic acid or a derivative thereof. By such a method, the reaction temperature can be controlled at extremely high precision and pressure fluctuations of the liquid phase reaction system can be suppressed (or restrained) significantly as well. For example, the temperature of the reaction system can be controlled within a range of ±0.5° C. with respect to a reference temperature. The reference temperature may be 150 to 220° C.

The control apparatus (stabilization apparatus) of this invention is equipped with the above-described liquid phase reaction system, a separation unit such as a distillation column, a temperature control unit for controlling the temperature of the separated component that has been separated by the separation unit, and a circulation line for circulating or returning the separated component that has been adjusted in temperature by the temperature control unit to the reaction system. This apparatus is also equipped with a flow rate sensor (or flow sensor) for detecting the circulation rate (return flow rate) of the separated component in the above-mentioned circulation line, a temperature sensor for detecting the temperature of the separated component in the above-mentioned circulation line, and a control unit, by means of the temperature control unit and based on the detection data from the flow rate sensor and temperature sensor, for controlling the heat quantity of the separated component that is circulated or returned to the reaction system. With the above-described apparatus, separation into a low boiling point component and a high boiling point component is carried out by the separation unit, and the high boiling point component is circulated or returned via the circulation line (first circulation line) to the reaction system. The separated low boiling point component can then be separated by a refining unit into a second low boiling point component, a component containing a carboxylic acid, and a second high boiling point component, and the second low boiling point component may be circulated or returned to the reaction system via a second circulation line. The above-described liquid phase reaction system may be practically a liquid phase exothermic reaction system without (that is not equipped with) a cooling unit, and the control unit may serve as a unit that controls the heat quantity of the separated component that is lower in temperature than the reaction system by means of the temperature control unit and controls the reaction temperature by the circulation rate (return flow rate) of the circulated separated component.

With the present specification, the expression "maintaining a substantially constant liquid level of the reaction system" means that the liquid level (the height level of the liquid surface) is maintained substantially constant on the average. That is, this expression shall not be limited to the case where the liquid level is maintained statically at a constant level, and it is sufficient for the liquid level to be substantially constant on the average even in the case where the liquid level fluctuates due to sparging of a gaseous component, etc.

BEST MODE FOR CARRYING OUT THE INVENTION

Figure 1:
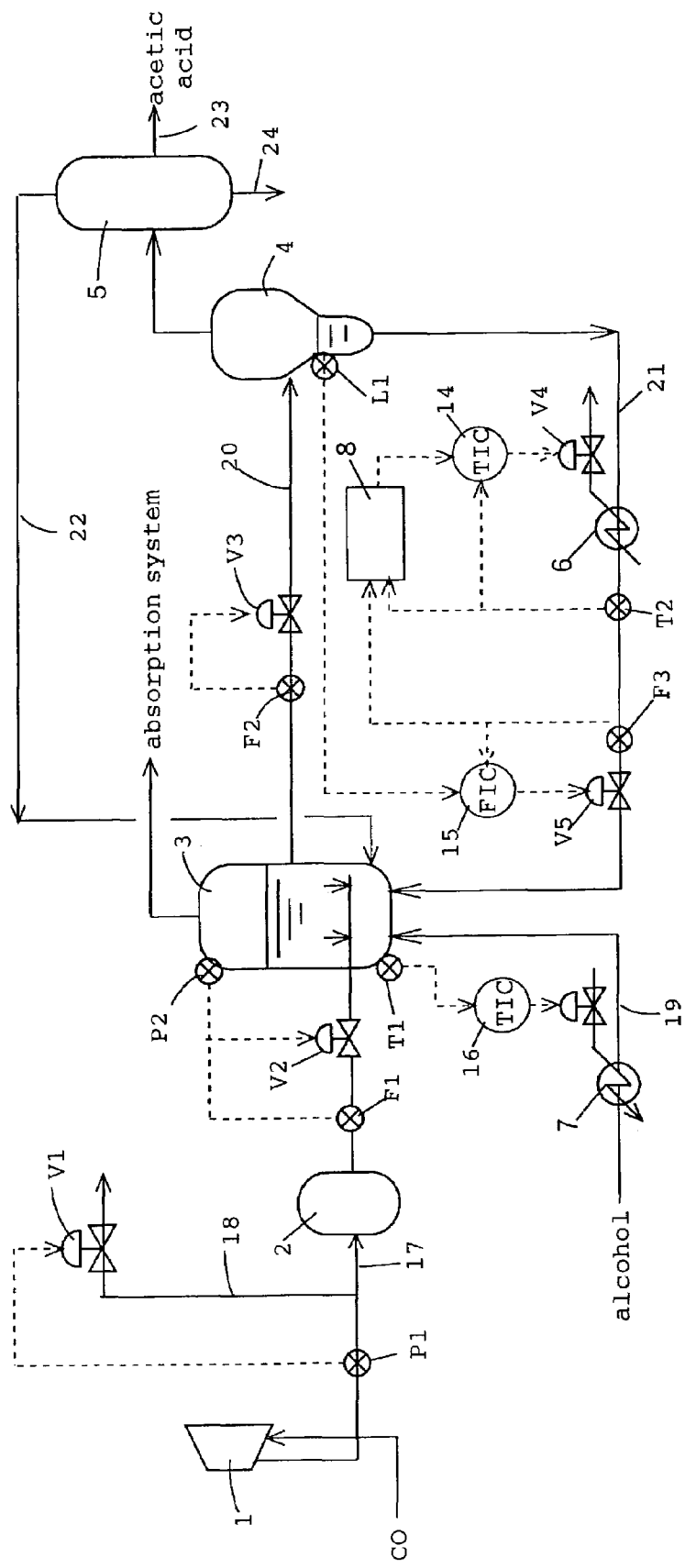
FIG. 1 shows a process flow diagram for explaining a reaction control method and control apparatus of this invention.
Figure 2:
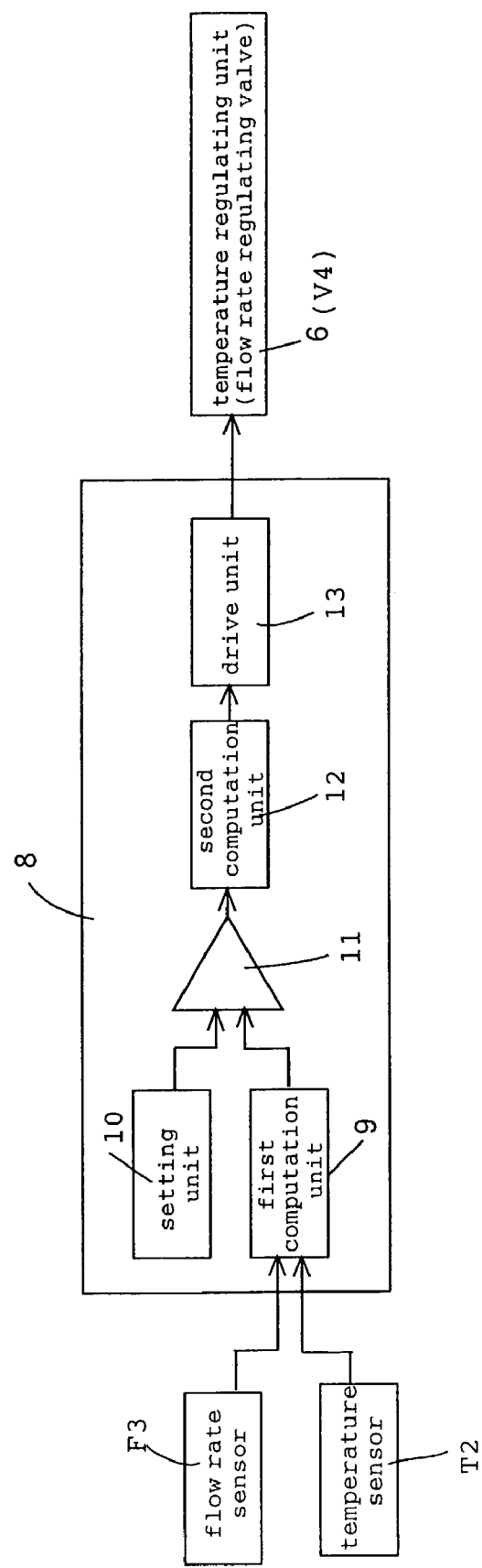
FIG. 2 is a block diagram for explaining the control apparatus of FIG. 1.

The present invention shall now be described in detail with reference as necessary to the attached drawings. FIG. 1 is a process flow diagram for explaining a control method and control apparatus of this invention. FIG. 2 is a block diagram for explaining the control apparatus of FIG. 1.

This embodiment illustrates a process for producing a carboxylic acid (such as acetic acid, etc.) by a carbonylation reaction of an alcohol (such as methanol, etc.) and carbon monoxide in the presence of a carbonylation catalytic system comprising a rhodium catalyst, lithium iodide, and methyl iodide.

This process is equipped with a compressor 1 for pressurizing the carbon monoxide as the gaseous reaction component (reactant), a feed line 17 for supplying or feeding the pressurized carbon monoxide continuously at a predetermined rate to a reactor 3 via a buffer tank 2, a feed line 19 for supplying the alcohol (methanol, etc.) as the liquid reaction component (reactant) continuously at a predetermined rate to the reactor 3, and a feed line 20 for continuously drawing out from the reactor part of the reaction mixture, which contains the carbonylation product (a carboxylic acid, such as acetic acid or a derivative thereof) produced by the reaction, with maintaining a substantially constant liquid level of the reactor 3, to supply the drawn the reaction mixture (the draw stream) to a flash distillation column 4, which serves as the separation unit. The reactor 3 comprises a liquid phase reaction system that includes the carbonylation catalytic system (a catalytic system comprising a principal or main catalytic component, such as rhodium catalyst, etc., and cocatalysts, such as lithium iodide and methyl iodide, etc.), and the carbon monoxide, which is the gaseous reactant, is sparged from the lower part or bottom of the reactor 3. Such a liquid phase reaction system (or reactor) is an exothermic reaction system (or reactor) accompanying with exothermic reaction. The above-described reactor 3 may be equipped with a heat removal unit or a cooling unit for controlling the reaction temperature, while is preferably not equipped with a heat removal unit or a cooling unit.

The gaseous component from the reactor 3 contains unreacted carbon monoxide, methyl iodide as the cocatalyst, byproduct methane, etc. This gaseous component containing such components is supplied from the above-described reactor 3 to an absorption system for recovery of the cocatalyst, such as methyl iodide, etc., and the recovered cocatalyst can then be reused in the reaction.

An exhaust line 18, for discharging while combusting the excess carbon monoxide that could not be absorbed at the above-mentioned buffer tank 2, is connected to the carbon monoxide feed line 17 at the upstream side of the buffer tank 2.

A pressure sensor (or flow rate sensor) P1, for detecting the feed pressure (or flow rate) of carbon monoxide, and a pressure regulating valve (electromagnetic valve) V1, for discharging excess carbon monoxide from the above-mentioned exhaust line 18 based on the data detected by the sensor and data concerning a reference value, are attached to the carbon monoxide feed line 17 at the upstream side of the buffer tank 2. Furthermore, a flow rate sensor (or pressure sensor) F1 and a flow rate regulating valve (or pressure regulating valve) V2 are mounted onto the carbon monoxide feed line 17 between the buffer tank 2 and the reactor 3, and a pressure sensor P2, for detecting the pressure of the gas phase in reactor 3, is mounted onto the upper part of the reactor 3. The flow rate of carbon monoxide into the reactor 3 is thus controlled by the flow rate regulating valve V2 based on the data detected by the flow rate sensor F1 of the carbon monoxide feed line 17 and the pressure sensor P2 of the reactor 3. Incidentally, a temperature sensor T1 for detecting the reaction temperature is mounted onto the reactor 3. The detection data from this temperature sensor T1 are transmitted to a temperature control unit 16, and this temperature control unit adjusts, by means of a temperature regulating unit (heat exchanger) 7 mounted onto an alcohol feed line 19, the temperature of the alcohol (methanol, etc.) that is supplied to the reactor 3. That is, in order to suppress the fluctuation of the temperature in the reactor 3 in a supplementary manner by means of the temperature of the raw material from the raw material feeding system, the alcohol (methanol, etc.) in the alcohol feed line 19 is fed to the reactor 3 upon lowering the temperature of the alcohol (methanol, etc.) by use of the temperature sensor T1, the temperature control unit 16 and the temperature regulating unit (heat exchanger) 7 when the temperature of the reactor 3 has become higher than the reference temperature, and upon raising the temperature of the alcohol (methanol, etc.) by means of the temperature regulating unit (heat exchanger) 7 when the temperature of the reactor 3 has become lower than the reference temperature.

Furthermore, the feed line 20, for supplying the reaction mixture solution from the reactor 3 to the flash distillation column 4, is provided with a flow rate sensor F2, for detecting the flow rate of the reaction mixture solution, and a flow rate regulating valve V3, for controlling the flow rate of the reaction mixture solution based on the detection data from this flow rate sensor.

At the above-mentioned flash distillation column 4, separation into a first low boiling point component (vapor component) containing the carbonylation product, and a first high boiling point component (liquid component) containing the carbonylation catalytic system (a rhodium catalyst, lithium iodide, and other high boiling point cocatalytic components) is carried out and the high boiling point component is circulated or returned to the reactor 3 through a first circulation line 21 while maintaining a substantially constant liquid level in the distillation column 4. Due to the latent heat of vaporization that accompanies the flash distillation, the temperature of the high boiling point component that is circulated or returned to the reactor 3 via the first circulation line 21 is lower than the reaction temperature (reference temperature) of the reactor 3.

The first low boiling point component (vapor component) that has been separated at flash distillation column 4 practically contains, in addition to the reaction product (acetic acid or other carboxylic acid), unreacted low boiling point reactants (an alcohol such as methanol), intermediate products (a carboxylic acid ester such as methyl acetate), volatile cocatalytic components (an alkane halide such as methyl iodide), and low boiling point byproducts. The first low boiling point component that has been separated in the separation step is thus supplied to a second separation step or refining system (for example, a fractionating column 5) and separated there into a second low boiling point component, which contains volatile cocatalytic components (methyl iodide, etc.) which are useful for the reaction, a carboxylic acid (acetic acid, etc.), and a second high boiling point component, as a result the refined carboxylic acid (acetic acid, etc.) is taken out via a line 23. Meanwhile, the second low boiling point component that has been separated at the fractionating column 5 is returned through a second circulation line 22 to the reactor 3, and the high boiling point component that has been separated at the fractionating column 5 is taken out through a line 24 from the column bottom. The temperature of the second low boiling point component that is returned to the reactor 3 is also usually lower than the reaction temperature (reference temperature) of the reactor 3.

A level sensor L1, for detecting the height of the liquid level of the liquid phase, is mounted onto the lower part of the flash distillation column 4. Furthermore a temperature sensor T2, for detecting the temperature of the first high boiling point component (liquid component) that is returned to the reaction system, and a flow rate sensor F3, for detecting the flow rate of the first high boiling point component, are mounted onto the circulation line 21. The detection data from this temperature sensor T2 are sent or transmitted to the control unit 14, and this control unit controls the temperature of the high boiling point component by means of a heat medium flow rate regulating valve V4 and a temperature control unit (heat exchanger) 6, provided at the first circulation line 21. Furthermore, the detection data with respect to the height of the liquid level provided by the above-mentioned level sensor L1 and the detection data from the above-mentioned flow rate sensor F3 are transmitted or provided to the control unit 15, and based on these detection data, this control unit controls the circulation rate (return flow rate) of the high boiling point component by means of the flow rate regulating valve V5 provided in the first circulation line 21 to thereby maintain the liquid level at the flash distillation column 4 at a predetermined height position.

With such a system, the temperature and/or pressure of the above-mentioned reactor 3 fluctuates as a result of fluctuation of at least one quantitative factor selected from the quantity (or amount) of the reaction mixture supplied from the reactor 3 to the flash distillation column 4 and the quantity of the high boiling point component circulated from the flash distillation column 4 to the reactor 3. In particular, not only is the reaction system a circulating system, in which a certain fluctuation or one of fluctuations (flow rate fluctuation) spreads successively to subsequent steps (in other words, a fluctuation propagating type circulating system) which may be accompanied with regular or irregular pulsating flow or variations, but the reaction system is one that is an exothermic reaction, and though the reactor 3 may be equipped with a heat removal or cooling unit, such as a jacket, the reactor 3 is preferably an open cooling type reaction system that is not equipped with a heat removal or cooling unit, such as a jacket. Moreover, the temperature of the reaction system is controlled by circulation or returning of the separated components that are lower in temperature than the reaction system. Thus with such a system, the temperature and pressure fluctuations of the reaction system are large. For example, if in the above-described system, a cascade control is performed utilizing the level sensor L1 to maintain the height position of the liquid level of the flash distillation column 4 at a predetermined position, the rate of draw-out (circulation rate or return rate) from the distillation column 4 to the reactor 3 will fluctuate, the enthalpy introduced into the reactor 3 will change and thus the temperature in the reactor 3 will fluctuate accordingly. Furthermore, due to the temperature change in the pressurized reactor 3, the pressure and carbon monoxide usage rate (or consumption rate) in reactor 3 will fluctuate. Stable operation of the reaction system is thus difficult and since the amount of carbon monoxide discharged from the exhaust line 18 will also be large, the carbon monoxide cannot be used effectively in the carbonylation reaction.

More specifically, an acetic acid production plant can be run under conditions, for example, of a reaction temperature (reference temperature) of about 150 to 220° C. (preferably about 170 to 200° C. and more preferably about 175 to 195° C.) and a high boiling point component temperature as controlled by the temperature regulating unit 6 of about 20 to 130° C. (preferably about 50 to 130° C., more preferably about 90 to 125° C., and especially about 100 to 125° C.). Also, the flow rate (flashed solution flow rate) of the reaction mixture at the feed line 20 corresponds substantially to the feed rate of the reaction components that are supplied to the reaction system, and relative to a flow rate (flashed solution flow rate) of the reaction mixture at the feed line 20 of 100 parts by volume/hour, the flow rate of the first high boiling point component at the first circulation line 21 is for example about 10 to 90 parts by volume/hour (preferably about 30 to 90 parts by volume/hour, more preferably about 50 to 80 parts by volume/hour, and especially about 60 to 70 parts by volume/hour), and the flow rate of the first low boiling point component that vaporizes from the flash distillation column 4 and is supplied to the refining step is for example about 10 to 90 parts by volume/hour (preferably about 20 to 70 parts by volume/hour, more preferably about 20 to 50 parts by volume/hour, and especially about 30 to 40 parts by volume/hour). Furthermore, relative to a flow rate (flashed solution flow rate) of the reaction mixture at the feed line 20 of 100 parts by volume/hour, the flow rate of the second low boiling point component at the second circulation line 22 is for example about 1 to 90 parts by volume/hour (preferably about 5 to 50 parts by volume/hour, more preferably about 5 to 20 parts by volume/hour, and especially about 10 to 15 parts by volume/hour).

However, even if the plant is operated under such conditions, not only does the flow rate of the reaction mixture at the feed line 20 fluctuate but since the height position of the liquid level at the flash distillation column 4 is controlled by the level sensor L1, the flow rate of the high boiling point component at the first circulation line 21 and the flow rate of the low boiling point component at the second circulation line 22 fluctuate and consequently, the temperature in the reactor 3 fluctuates for example within a range of about ±0.5 to 1° C. with respect to the reference temperature.

Thus according to the present invention, the detection data from the flow rate sensor F3 and the temperature sensor T2 at the above-mentioned first circulation line 21 are provided or transmitted to a control unit (or control device) 8, and the temperature of the high boiling point component that is returned to the reaction system is controlled according to the heat quantity of the high boiling point component based on the flow rate and temperature. More specifically, the flow rate data from the flow rate sensor F3 and the temperature data from the temperature sensor T2 at the circulation line 21 are transmitted to the control unit 8 as shown in FIG. 2. The control unit (or control device) 8 comprises a first computation or calculating unit 9, which computes or calculates the heat quantity data for the circulated high boiling point component based on the above-mentioned flow rate data and temperature data, a comparison unit 11, which compares a reference heat quantity data (threshold data) that is set at a setting unit 10 and serves as a reference for maintaining the temperature in the above-mentioned reactor 3 at a predetermined temperature with the calculated heat quantity data, a second computation or calculating unit 12, which computes or calculates a control amount with respect to the temperature based on the deviation between the heat quantity data and the reference heat quantity data calculated by the comparison unit when the heat quantity data deviates from the threshold value of the reference heat quantity data, and a drive unit 13, which, based on the control amount concerning temperature that is calculated by the second computation unit, controls the temperature of the circulated high boiling point component by means of the above-mentioned heat medium flow rate regulating valve V4 and temperature regulating unit 6. With the temperature regulating unit 6 of the present embodiment, the signal with respect to the control amount from the drive unit 13 is transmitted to the above-mentioned flow rate regulating valve V4 for controlling the flow rate of the heat medium.

With a process equipped with such a control device, even when the circulation rate (return rate) of the high boiling point component in the first circulation line 21 fluctuates, since the heat quantity of the circulated high boiling point component is controlled in accordance with (or in response to) the circulation rate (return rate) of the high boiling point component that occupies a large portion of the flows returned to the reaction system, temperature fluctuations and pressure fluctuations within the reactor 3 can be suppressed significantly and the acetic acid production process can be stabilized. For example, when acetic acid is industrially produced under the conditions of the above-described acetic acid production plant, the temperature of the reaction system can be controlled in an extremely stable manner with respect to the reference temperature, that is for example, within a range of reference temperature ±0.5° C. (preferably within a range of reference temperature ±0.3° C. and especially within a range of reference temperature ±0.2° C.). Furthermore, since temperature and pressure fluctuations (variations) can be suppressed or inhibited and the reaction system can be stabilized, not only the carbon monoxide feed rate and methanol feed rate but the acetic acid production rate can also be increased. Furthermore, the discharge rate of carbon monoxide from the exhaust line 18 can be reduced and the carbon monoxide can thus be utilized effectively in the carbonylation reaction.

This invention can be applied not just to the above-described case of a continuous carboxylic acid production process but to any process (for example, a continuous production process) wherein while supplying reactants (gaseous reaction components, liquid reaction components, etc.) continuously at a prescribed rate into a liquid-phase reaction system, part of the reaction product of the reaction system is subjected continuously to a separation step or separation system (distillation column, etc.), and the separated component (low boiling point component or high boiling point component) that has been separated in the separation step is circulated or returned to the above-mentioned reaction system. This invention enables stabilization of a liquid phase reaction system especially in the case of application to a system with which at least one flow rate (return flow rate), among the feed rate of the reaction product from the reaction system to a separation system (distillation system, etc.) and the circulation rate (return flow rate) of the separated component (such as a high boiling point component, etc.) from the separation system (distillation system, etc.) to the reaction system, fluctuates (and especially a system with which the circulation rate of the separated component from the separation system to the reaction system fluctuates with or without a pulsating mode).

Furthermore, this invention is favorably applied to an exothermic reaction system, which is not equipped with a heat removal unit or cooling unit using a coolant, etc., and with which the temperature of the reaction system is controlled by the temperature and flow rate of a separated component that is lower in temperature than the reaction system (an exothermic reaction system using open cooling). The temperature of the separated component that is circulated or returned to the reaction system can be selected from among temperatures that are for example about 10 to 120° C. (and especially about 20 to 100° C.) lower than the reference temperature of the reaction system and is usually about 30 to 100° C. (for example, about 50 to 80° C.) lower than the reference temperature of the reaction system.

The separated component that is circulated or returned to the reaction system can be selected according to the type of reaction and usually contains an effective component for the reaction. This effective component includes not only catalytic components but also unreacted reaction components, reaction solvents, etc. The separated component that is circulated or returned to the reaction system is practically a liquid. Furthermore, the separated component that is separated by the separation system and contains the object compound is usually not returned to the reaction system but is supplied to the separation refining system for recovery of the object compound.

Furthermore, this invention can be applied to various liquid phase reactions (e.g., a pressurized liquid phase reaction) with which catalytic components and other effective components are returned to the reaction system, with examples including carbonylation reactions, disproportionation reactions (production of toluene and trimethylbenzene from xylene, etc.), isomerization reactions (production of fumaric acid from maleic acid, etc.), metathesis reactions, hydration reactions, hydroformylation reactions, esterification reactions, oxidation reactions, condensation reactions, halogenation reactions, etc. The reaction components can be selected according to the type of reaction and are not restricted in particular.

For instance, examples of components that are used in carbonylation reactions include combinations of an alcohol (methanol, etc.) or a derivative thereof and carbon monoxide (production of acetic acid or other carboxylic acid or derivative thereof), combinations of an olefin (ethylene, etc.), carbon monoxide, and hydrogen (production of acetaldehyde or other aldehyde), combinations of an olefin, carbon monoxide, and water (production of a carboxylic acid), combinations of an olefin, carbon monoxide, and an alcohol (production of a carboxylic acid ester), combinations of an alkyne (acetylene, methyl acetylene, etc.), carbon monoxide, and water (production of acrylic acid, methacrylic acid, or other unsaturated carboxylic acid), combinations of an alkyne (acetylene, methyl acetylene, etc.), carbon monoxide, and an alcohol (methanol, etc.) (production of methyl acrylate, methyl methacrylate, or other unsaturated carboxylic acid ester), combinations of an alcohol, carbon monoxide, and oxygen (production of a diester carbonate, etc.)

Examples of an alcohol used in the above-mentioned carbonylation reaction include $C_{1-10}$ alkyl alcohols, such as methanol, ethanol, propanol, isopropanol, butanol, pentanol, hexanol, $C_{3-10}$ cycloalkyl alcohols, such as cyclohexanol, cyclooctanol, etc., phenols, such as phenol, etc., and aralkyl alcohols, such as benzyl alcohol, phenethyl alcohol, etc. Examples of alcohol derivatives include esters, such as methyl acetate, ethyl acetate, and other $C_{2-6}$ alkyl carboxylic acid—$C_{1-6}$ alkyl esters, and halides, such as methyl iodide, ethyl iodide, propyl iodide, and other $C_{1-10}$ alkyl iodides as well as bromides (methyl bromide, propyl bromide, etc.) and chlorides (methyl chloride, etc.) corresponding to such alkyl iodides. Examples of ethers include $C_{1-6}$ alkyl ethers, such as methyl ether, ethyl ether, propyl ether, isopropyl ether, butyl ether, etc. If necessary, as the alcohol, a polyvalent alcohol, for example, an alkylene glycol, such as ethylene glycol, propylene glycol, butane diol, etc., or a derivative (for example, an ester, halide, ether, etc.) of such a polyvalent alcohol may be used.

Examples of olefins include alkenes, such as ethylene, propylene, butene-1, butene-2, hexene, octene, etc., cycloalkenes, such as cyclohexene, methyl cyclohexene, etc., and dienes, such as allene, butadiene, isoprene, etc. Examples of alkynes include acetylene, methyl acetylene, etc.

A preferable liquid phase reaction system is a reaction system to obtain a carboxylic acid or a derivative thereof (such as a carboxylic acid anhydride, etc.) by using an alcohol, preferably a $C_{1-4}$ alcohol or a derivative thereof (for example, methanol, methyl acetate, methyl iodide, dimethyl ether, etc.) as the liquid reaction component, and in particular, a reaction system to produce acetic acid or a derivative thereof by reacting methanol with carbon monoxide in a liquid phase reaction system in the presence of a carbonylation catalyst.

With the above-mentioned liquid phase reaction system, the reaction may be carried out in the presence of a catalyst or a catalytic system, and though the catalyst or catalytic system is not restricted in particular and may be selected in association with the type of reaction, a high boiling point catalyst or metal catalyst is usually used in the above-mentioned carbonylation reaction. For example, examples of the above-mentioned carbonylation catalyst include transition metal catalysts, such as rhodium catalyst, iridium catalyst, platinum catalyst, palladium catalyst, copper catalyst, osmium catalyst, nickel catalyst, cobalt catalyst, etc. The catalyst may be the simple metal (or elemental metal) or may be used in various forms such as metal oxide (including composite oxides), hydroxide, halide (chloride, bromide, iodide, etc.), carboxylate (acetate, etc.), inorganic acid salt (sulfate, nitrate, phosphate, etc.), complex, etc.

The concentration of the catalyst may be selected according to the type of liquid phase reaction, and for example in the case of the above-mentioned carbonylation reaction, the concentration of the catalyst in weight with respect to the entirety of the liquid phase system is about 5 to 10000 ppm, preferably about 10 to 7000 ppm, and more preferably about 20 to 5000 ppm (for example, about 50 to 1000 ppm).

The carbonylation catalyst may also be combined with a cocatalyst or promoter and used as a catalytic system. The cocatalyst or promoter may be selected depending on the type of reaction, and examples in the case of production of a carboxylic acid by a carbonylation reaction of an alcohol include alkali metal halides (for example, lithium iodide, potassium iodide, sodium iodide, lithium bromide, etc.), hydrogen halides (hydrogen iodide, hydrogen bromide, etc.), alkyl halides (methyl iodide, methyl bromide and other $C_{1-4}$ alkane halides), etc. An alkali metal halide also functions as a stabilizer for a carbonylation catalyst (for example, rhodium catalyst, etc.). Also for the production of (meth) acrylic acid or an ester thereof, etc., an amine (a chain or cyclic tertiary amine, etc.) or an organic sulfonic acid (an alkyl sulfonic acid, such as methanesulfonic acid or a salt thereof, etc.), etc., may be used.

The content of the cocatalyst or promoter can be selected according to the type of liquid phase reaction, and for example in the case of the above-described carbonylation reaction, the content of each component with respect to the entirety of the liquid phase system is about 0.1 to 30 weight %, preferably about 0.5 to 20 weight %, and more preferably about 1 to 15 weight %. More specifically, for the above-mentioned production of a carboxylic acid by carbonylation reaction of alcohol, the content of methyl iodide or other alkane halide with respect to the entirety of the liquid phase system is about 0.1 to 25 weight %, preferably about 1 to 20 weight %, and more preferably about 5 to 15 weight % and the content of lithium iodide or other alkali metal halide with respect to the entirety of the liquid phase system is about 0.1 to 30 weight %, preferably about 0.5 to 15 weight %, and more preferably about 1 to 10 weight %.

For the production of a carboxylic acid by carbonylation of an alcohol, methyl acetate or other carboxylic acid ester (especially an ester of the carboxylic acid to be produced with an alcohol) may be contained at an amount with respect to the entirety of the liquid phase system of about 0.1 to 75 weight %, preferably about 0.2 to 50 weight % (for example, 0.2 to 25 weight %), and more preferably about 0.5 to 10 weight % (for example, 0.5 to 5 weight %).

The carbon monoxide may be used as a pure gas or may be used upon dilution with an inert gas (for example, nitrogen, helium, carbon dioxide, etc.). The partial pressure of carbon monoxide in the reaction system may be selected suitably according to the type of reaction, etc., and for example for the production of a carboxylic acid by carbonylation reaction of an alcohol, the partial pressure of carbon monoxide in the reaction system is, for example, about 200 to 3000 kPa, preferably about 400 to 1500 kPa, and more preferably about 500 to 1000 kPa.

The reaction may be carried out in the presence or absence of a solvent or may be carried out in the presence of hydrogen gas and/or water (for example of an amount with respect to the entirety of the liquid phase system of about 0.1 to 30 weight %, preferably about 0.5 to 15 weight %, and more preferably about 1 to 10 weight %).

The reaction temperature and pressure of the carbonylation reaction may be selected suitably according to the type of liquid phase reaction and for example, the reaction temperature may be about 100 to 250° C. (preferably about 150 to 220° C. and more preferably about 170 to 200° C.) and the reaction pressure may be about 1000 to 5000 kPa (for example, about 1500 to 4000 kPa).

With such a liquid phase reaction system that the height of the liquid level is comparatively stable, a level sensor, for detection of the height of the liquid level of the liquid phase reaction system, may be mounted as necessary to the reactor in order to control the height of the liquid level in the reactor.

In the above-mentioned carbonylation reaction of an alcohol, in addition to the production of the carboxylic acid (acetic acid, etc.) corresponding to the alcohol (methanol, etc.), the ester (methyl acetate, etc.) of the produced carboxylic acid with the alcohol is produced and water, etc., are also produced in accompaniment with the esterification reaction.

Instead of being subjected directly to the separation step, the reaction product (reaction mixture solution) may be pretreated (subjected to filtration treatment, etc.), cooled to a predetermined temperature, and then subjected to the separation step. In the separation step, the reaction product (reaction mixture solution) may be separated into a vapor component as the low boiling point component that contains the reaction product, and a liquid component as the high boiling point component, by a separation zone (for example, a separation unit, such as a distillation column, etc.) that is practically lower in pressure than the reaction zone. As a separation unit, various separation means, such as a distillation column (plate column, packed column, flash distillation column, etc.) may be used. At the separation unit, heating may be performed or separation into the vapor component and the liquid component may be carried out without heating. For example, in cases where flash distillation is to be utilized, the reaction mixture can be separated by depressurization without heating in an adiabatic flash distillation step, the reaction mixture can be separated by heating and depressurization of the reaction mixture in an isothermal flash distillation step, or these flash conditions may be combined to separate the reaction mixture. Such flash distillation may be performed on a reaction mixture for example at a temperature of about 80 to 200° C. and a pressure of about 50 to 1000 kPa (for example, about 100 to 1000 kPa).

In this invention, usually, a separated component A, which contains effective components useful for the reaction, and a separated component B, which mainly contains the object compound, are separated from the reaction product (reaction mixture), and the separated component A is returned to the reaction system for efficient use of the effective components and the object compound is separated and refined from the separated component B. Thus in the case where the first high boiling point component and/or the first low boiling point component mainly contain the object compound and the effective components (catalytic components, etc.), the first high boiling point component and/or the first low boiling point component may be supplied to a separation refining system (or refining system) and separated into the object compound and the component containing effective components, and the component containing effective components may then be circulated to the reaction system. The object compound may be refined not just by distillation or fractionation but also by absorption, adsorption, condensation, crystallization, or other techniques.

The first high boiling point component and/or the second high boiling point component may contain high boiling point byproducts in some cases. Also, the first low boiling point component and/or the second low boiling point component may contain low boiling point byproducts in some cases. Thus the high boiling point byproducts or low boiling point byproducts may be separated if necessary from such high boiling point or low boiling point components, and in cases where components that are effective to the reaction are contained, the component containing effective components may be circulated to the reaction system. Further, as has been disclosed in Japanese Patent Application Laid-open No. 321847/1994 (JP-6-321847A), a high boiling point component may be made to contain water (at an amount for example of about 0.5 to 30 weight % and preferably about 1 to 15 weight %) for preventing precipitation or sedimentation (or deposition) and stabilizing the catalytic system.

The first separation step (separation unit) and/or the second separation refining step (refining unit) may each be arranged as a single step (or unit) or as a plurality of steps (or units).

In this invention, in order to stabilize the temperature and/or pressure of the liquid phase reaction system, the heat quantity of a circulated component is controlled in association with (or according to) the circulation rate (or return flow rate) of the separated component (circulated component or returned component) from the separation step. The heat quantity of the separated component can be controlled by detecting the flow rate (return rate) and temperature of the circulated component and controlling the temperature of the circulated component based on the detected flow rate and temperature. In the case where the width of fluctuation of the temperature of the circulated component is small, the flow rate of the circulated component may be detected and the temperature of the circulated component may be controlled based on the detected flow rate data. By such control, the temperature of the above-described reaction system can be controlled at a predetermined temperature and pressure fluctuations of the gas phase of the reaction system can be suppressed or restrained. More specifically, when T1 represents a reference temperature (reference value regarding temperature) of the reaction system, A1 represents a reference circulation rate (reference value regarding the circulation rate or flow rate) of the circulated component, A2 is a circulation rate (flow rate) of the circulated component, and T2 indicates a temperature of the circulated component, it is useful to control the heat quantity of the circulated high boiling point component in accordance with the return rate (or return amount) of the circulated component by controlling the temperature of the circulated component, based on the difference $\Delta(A1-A2)$ of the above-mentioned circulation rates (flow rates) and the temperature difference $\Delta(T1-T2)$ of the circulated component.

Though in the above-described example, the temperature of the reaction system is controlled by controlling the heat quantity of the first high boiling point component, the heat quantity of the second low boiling point component that is circulated to the reaction system may also be controlled to control or regulate the temperature of the reaction system even more precisely. For example, the flow rate and temperature of the second low boiling point component may be detected by means of a flow rate sensor and a temperature sensor in the second circulation line and the temperature of the circulated second low boiling point component (the heat quantity of the second low boiling point component) may be controlled based on the detection data from the flow rate sensor and temperature sensor by the same control unit and temperature control unit as described above to control the temperature of the above-mentioned reaction system at a predetermined temperature and to restrain pressure fluctuations of the gas phase of the above-mentioned reaction system.

Various modes or forms of feedback control and other of process control actions may be used for control of the heat quantity of the circulated component (or returned component), and examples of such process control actions include a proportional control action (P control action), with which the manipulated variable is controlled in proportion to the deviation of the heat quantity from the reference heat quantity, an integral control action (I control action), with which the manipulated variable is controlled by or upon integrating the heat quantity deviation, a differential control action (D control action), with which the manipulated variable is controlled in accordance with the variation of the heat quantity deviation, and actions that combine the above modes (for example, a PI action, a PD action, and a PID action). For example, the I action may be utilized and the deviation of the return flow rate of a circulated component (in the above-described example, a returned component such as the first high boiling point component and/or the second low boiling point component) with respect to a reference flow rate may be integrated over each predetermined time period and the circulated component may be controlled in temperature and returned to the reaction system when the integrated amount of the return flow rate deviation reaches a predetermined flow rate.

The circulated component may be cooled to a predetermined temperature, the temperature of the circulated component may be adjusted to a predetermined temperature utilizing the above-described control unit and temperature regulating unit, and the temperature-controlled circulated component may be circulated to the reactor at a predetermined rate. In such an embodiment, the temperature of the circulated component may be controlled based on the above-mentioned circulation rate (flow rate) difference Δ(A1−A2) without controlling the temperature of the circulated component based on the temperature difference Δ(T1−T2) of the circulated component. Futher, the circulated component (the liquid component containing the carbonylation catalytic system, etc.) may be controlled to be approximately the same in temperature as the reaction temperature of the reaction system and then circulated to the reaction system.

In the circulation line, the temperature regulating unit may be mounted at the downstream side of the flow rate sensor and the temperature sensor. As long as the above-described control unit is utilized, a buffer tank for temporary storage of the circulated component may be provided as necessary in the circulation line.

Though in the above-described embodiment, the reaction product of the reactor is supplied to the separation unit by a single feed line and the circulated liquid component that has been separated by the separation unit is returned to the reaction system by a single first or second circulation line, the reaction product of the reactor may also be supplied to the separation unit through a plurality of feed lines (for example, a main feed line and a bypass line). Further, the circulated component that has been separated by the separation unit may be returned to the reaction system through a plurality of circulation lines. In the case where a plurality of circulation lines are utilized, it is sufficient that the heat quantity of the entirety of the circulated component is controlled utilizing at least one of the circulation lines, and for example, while returning the circulated components constantly to the reaction system by a main circulation line, a temperature regulating unit may be mounted onto a bypass line to control the heat quantity of the entirety of the circulated component that is circulated to the reaction system based on the flow data and temperature data.

With respect to the temperature regulating unit, a cooling water or other coolant may be used, or a silicone oil or other heat medium that can be heated may be used. Furthermore, instead of just a single temperature regulating unit, a plurality of temperature regulating units may be mounted onto a circulation line.

INDUSTRIAL APPLICABILITY

According to the present invention, since the heat quantity is controlled in accordance with the circulation rate (return rate) of a high boiling point component to a reaction system, a liquid phase reaction system (carbonylation reaction system, etc.) can be stabilized effectively even when the circulation rate (return rate) of the high boiling point component fluctuates. Further, since temperature and pressure fluctuations of the reaction system can be restrained and the reaction system can thereby be stabilized, reaction components can be supplied in a stable manner and the reaction components can be utilized effectively to increase the production rate (or amount) of a object product. The object product can thus be produced stably with and industrial advantageous.

EXAMPLES

The following examples are intended to describe this invention in further detail and should by no means be construed as defining the scope of the invention.

Comparative Example

Using the apparatus shown in FIG. 1 without using the control unit 8 and temperature regulating unit 6 shown in FIG. 1 and FIG. 2, carbon monoxide was supplied from a carbon monoxide production plant to the reactor at a pressure of 3079 kPa, methanol was supplied to the reactor at a flow rate of about 29 kg/H, and reaction was carried out at a reference carbon monoxide partial pressure of 700 to 755 kPa, a reference pressure of 2755 kPa, and a reference temperature of 187.5° C. For methanol, the operation of heating when the temperature of the reactor dropped below the reference temperature or cooling when the temperature of the reactor became higher than the reference temperature was carried out to adjust the temperature of methanol for supplying to the reactor. When the pressure of carbon monoxide exceeded 3236 kPa, the excess carbon monoxide that could not be absorbed at the buffer tank was combusted at and discharged from the exhaust line. The reaction was carried out under a rhodium iodide concentration of 550 to 600 ppm, a methyl iodide concentration of 12 to 13 weight %, a lithium iodide concentration of 4.7 to 4.9 weight %, a methyl acetate concentration of 1.5 to 1.7 weight %, and a water concentration of 7.8 to 8.0 weight % in the liquid phase.

Part of the reaction mixture solution was supplied continuously from the reactor to the flash distillation column, flash distillation was performed at a reference pressure of 157 kPa, a reference temperature of 130° C., and a reference flash rate of 540 L/H, and the separated first high boiling point component (reference temperature: 122° C.) was circulated or returned to the reaction system at a reference flow rate of 350 L/H. Further, the first low boiling point component that was separated by flash distillation was supplied to a plurality of fractionating columns and the fraction containing methyl iodide and water (second low boiling point component) was circulated or returned without temperature regulation to the reaction system at a reference flow rate of 66 L/H.

When continuous production of acetic acid was carried out under the above conditions, the flow rate of carbon monoxide from the carbon monoxide production plant fluctuated in the range of 21.2 to 21.8 $Nm^3/H$, the methanol loading flow rate was 28.8 kg/H, and the methanol was supplied to the reactor with temperature regulation within a range of 60 to 100° C.

The reaction mixture having a temperature of 186.9 to 188.1° C. was supplied to the flash distillation column with the supply pressure fluctuating in the range of 2726 to 2785 kPa and the flow rate fluctuating in the range of 530 to 545 L/H. The first high boiling point component that was separated at the flash distillation column was circulated or returned to the reactor with the flow rate (return flow rate) fluctuating in the range of 345 to 355 L/H. Furthermore, the flow rate (return flow rate) of the second low boiling point component, which was separated at the fractionating columns and circulated to the reaction system, fluctuated in the range of 64.8 to 67.2 L/H.

Furthermore, the discharge rate of carbon monoxide from the exhaust line fluctuated in the range of 0 to 0.6 $Nm^3/H$ (discharge pressure: 3236 kPa), the reaction temperature fluctuated in the range of 186.9 to 188.1° C., and the reaction pressure also fluctuated in the range of 2726 to 2785 kPa.

The reaction mixture that was subjected to flash distillation contained 72 weight % of acetic acid, 13 weight % of methyl iodide, 2 weight % of methyl acetate, 8 weight % of water, 600 ppm of rhodium iodide, and 5 weight of lithium iodide. The high boiling point component separated at the distillation column contained 81 weight % of acetic acid, 2 weight % of methyl iodide, 1 weight % of methyl acetate, 9 weight % of water, 1000 ppm of rhodium iodide, and 7 weight % of lithium iodide. Also, the fraction (second low boiling point component) from the fractionating columns contained 61 weight % of acetic acid, 19 weight % of methyl iodide, 8 weight % of methyl acetate, and 12 weight % of water.

Example

With the exception of circulating the first high boiling point component, which was separated at the flash distillation column and was circulated to the reactor, to the reactor with regulating the temperature of the circulated high boiling point component by just 0.415° C. when the flow rate of the high boiling point component fluctuates by a proportion of 1 L/H, acetic acid was produced in the same manner as in the Comparative Example. That is, the control unit 8 and temperature regulating unit 6 shown in FIG. 1 were utilized and by an I action mode, the operation of raising the temperature of the high boiling point component by 0.415° C. from the reference temperature of 122° C. when the integral value of the flow rate of the first high boiling point component increased by 1 L/H relative to the reference flow rate of 350 L/H and lowering the temperature of the high boiling point component by 0.415° C. from the reference temperature of 122° C. when the integral value of the flow rate of the first high boiling point component decreased by 1 L/H relative to the reference flow rate of 350 L/H was performed.

When continuous production of acetic acid was carried out under the above conditions, the flow rate of carbon monoxide from the carbon monoxide production plant fluctuated within the narrow range of 21.7 to 21.8 $Nm^3/H$ and the methanol loading flow rate increased to 29.3 kg/H. The feed temperature of methanol was regulated within a range of 60 to 90° C. in supplying the methanol to the reactor.

The reaction mixture having a temperature of 187.5 to 187.8° C. was supplied to the flash distillation column with the supply pressure in the narrow range of 2750 to 2760 kPa and the flow rate in the narrow range of 537 to 542 L/H. The flow rate (return flow rate) of the first high boiling point component, which was separated at the flash distillation column and was circulated to the reactor, fluctuated in the narrow range of 347 to 352 L/H. Furthermore, the flow rate (return flow rate) of the second low boiling point component, which was separated at the fractionating columns and circulated to the reaction system, fluctuated in the range of 66 to 69 L/H.

Furthermore, the discharge rate of carbon monoxide from the exhaust line fluctuated in the range of 0 to 0.1 $Nm^3/H$ (discharge pressure: 3236 kPa), the fluctuation width of the reaction temperature was 187.5 to 187.6° C., and the fluctuation width of the reaction pressure was 2750 to 2760 kPa.

The compositions of the reaction mixture that was subjected to flash distillation, the high boiling point component that was separated at the distillation column, and the second low boiling point component from the fractionating columns were the same as the corresponding compositions of the Comparative Example.

As compared with the Comparative Example, the method of the Example shows that the fluctuation width of the temperature of the reaction system was significantly reduced from "reference temperature ±0.6° C." to "reference temperature ±0.1° C" and that the fluctuation width of the reaction pressure was significantly reduced from "reference pressure ±30 kPa" to "reference pressure ±5 kPa". Furthermore, in the Example, since the reaction system can be stabilized, not only the feed rate of carbon monoxide and the feed rate of methanol but the production rate of acetic acid can also be increased, moreover the discharge amount (or release amount) of carbon monoxide could be reduced significantly from "O to 6 L/H" to "0 to 0.1 L/H", and the carbon monoxide could be utilized effectively in the carbonylation reaction.

The results are shown in Table 1.

TABLE 1

| | | Comparative Example | Example |
|---|---|---|---|
| carbon monoxide | flow rate ($Nm^3/H$) | 21.2–21.8 | 21.7–21.8 |
| | pressure (kPa) | 3079 | 3079 |
| methanol | flow rate (kg/H) | 28.8 | 29.3 |
| | temperature (° C.) | 60–100 | 60–90 |
| flash solution | flow rate (L/H) | 530–545 | 537–542 |
| | temperature (° C.) | 187.1–187.8 | 187.5–187.6 |
| | pressure (kPa) | 2726–2785 | 2750–2760 |
| first high boiling point component | flow rate (L/H) | 345–355 | 347–352 |
| second low boiling point component | flow rate (L/H) | 64.8–67.2 | 66–69 |
| carbon monoxide discharge rate | flow rate ($Nm^3/H$) | 0–0.6 | 0–0.1 |
| reaction temperature | temperature(° C.) | 186.9–188.1 | 187.5–187.6 |
| reaction pressure | pressure (kPa) | 2726–2785 | 2750–2760 |

The invention claimed is:

1. A reaction control method comprising supplying reaction components continuously into a liquid phase reaction system, subjecting continuously part of the reaction product in the reaction system to a separation step and circulating a separated liquid component that has been separated in the separation step to said reaction system,
   wherein the reaction system is an exothermic reaction system, and the temperature of said reaction system is controlled in accordance with the following steps:
   (i) detecting a flow rate and temperature of the circulated separated liquid component from said separation step,
   (ii) calculating a heat quantity value of the circulated separated liquid component from said separation step, based on the flow rate and temperature detected in the detecting step (i), and
   (iii) regulating the heat quantity of the circulated separated liquid component returned to the reaction system by means of controlling the temperature of the circulated separated liquid component based on a deviation between the heat quantity value of the circulated separated liquid component calculated in step (ii) and a predetermined reference heat quantity value serving as a reference for maintaining the temperature in the reaction system at a predetermined temperature.

2. A reaction control method according to claim 1, wherein a separated liquid component containing catalytic components, unreacted reaction components, and reaction solvents for the reaction is circulated to the reaction system.

3. A reaction control method according to claim 1, wherein the reaction system temperature is controlled at a predetermined temperature for a system in which the rate of circulation of the separated component from the separation step to the reaction system fluctuates,
   which comprises detecting the flow rate and temperature of the circulated separated component, and regulating the temperature of the circulated separated component based on the detected flow rate and temperature.

4. A reaction control method according to claim 1, wherein the reaction system is an exothermic reaction system without a heat removal unit, and the temperature of the circulated separated component is lower in temperature than the reaction system.

5. A reaction control method according to claim 1 in which:

an alcohol and carbon monoxide are supplied into a liquid phase reaction system comprising a carbonylation catalytic system;

part of the reaction mixture, which comprises the carboxylic acid produced by the reaction, is drawn out from the reaction system with maintaining a substantially constant liquid level in the reaction system and is subjected to a flash distillation; and a high boiling point component is circulated to the reaction system, said high boiling point component comprises the carbonylation catalytic system and has been separated by the flash distillation from a low boiling point component comprising the carbonylation product, wherein the flow rate and temperature of the circulated high boiling point component are detected, and the temperature of the circulated high boiling point component is controlled based on the detected flow rate and temperature to control the temperature of said reaction system at a predetermined temperature and to suppress the pressure fluctuation of the gas phase of said reaction system.

6. A reaction control method according to claim 5, wherein the low boiling point component that has been separated by flash distillation is further subjected or supplied to a refining system for separation into a second low boiling point component, a component containing carboxylic acid, and a second high boiling point component, and the second low boiling point component that has been separated by the refining system is circulated to the reaction system.

7. A reaction control method according to claim 5, wherein the liquid phase reaction system is a reaction system in which methanol and carbon monoxide are reacted in the presence of a carbonylation catalytic system to produce acetic acid or a derivative thereof.

8. A reaction control method according to claim 5, wherein the high boiling point component contains a carbonylation catalytic system comprising a rhodium catalyst and a cocatalyst, and the low boiling point component contains a carboxylic acid, a carboxylic acid ester and an alkane halide.

9. A reaction control method according to claim 6, wherein the second low boiling point component contains an alkane halide.

10. A reaction control method according to claim 1, wherein the temperature of the reaction system is controlled within a range of $\pm 0.5°$ C. with respect to a reference temperature.

11. A reaction control method according to claim 10, wherein the reference temperature is 150 to 220° C.

12. A reaction control method according to claim 1, wherein the temperature of the circulated separated liquid component is controlled based on a deviation between the heat quantity value of the circulated separated liquid component and the reference heat quantity value when the heat quantity value deviates from the reference heat quantity value.

* * * * *